(12) United States Patent
Yang et al.

(10) Patent No.: US 8,268,597 B2
(45) Date of Patent: Sep. 18, 2012

(54) RECOMBINANT MICROORGANISM AND METHOD FOR PRODUCING L-LYSINE

(75) Inventors: Sheng Yang, Shanghai (CN); He Huang, Shanghai (CN); Dehui Wang, Changchun (CN)

(73) Assignee: Global Bio-Chem Technology Group Company Limited, Admiralty (HK)

( * ) Notice: Subject to any disclaimer, the term of this patent is extended or adjusted under 35 U.S.C. 154(b) by 660 days.

(21) Appl. No.: 12/395,976

(22) Filed: Mar. 2, 2009

(65) Prior Publication Data

US 2012/0107882 A1    May 3, 2012

Related U.S. Application Data

(60) Provisional application No. 61/033,099, filed on Mar. 3, 2008.

(51) Int. Cl.
*C12P 13/08* (2006.01)
*C07H 21/04* (2006.01)
*C07K 1/00* (2006.01)

(52) U.S. Cl. .................. 435/115; 536/23.1; 530/350

(58) Field of Classification Search .................. None
See application file for complete search history.

(56) References Cited

U.S. PATENT DOCUMENTS

| | | | |
|---|---|---|---|
| 4,327,118 A | 4/1982 | Georgen et al. | |
| 4,346,170 A | 8/1982 | Sano et al. | |
| 5,650,304 A | 7/1997 | Ishii et al. | |
| 5,827,698 A | 10/1998 | Kikuchi et al. | |
| 5,932,453 A | 8/1999 | Kikuchi et al. | |
| 5,989,875 A | 11/1999 | Kojima et al. | |
| 6,017,555 A | 1/2000 | Stevens et al. | |
| 6,040,160 A | 3/2000 | Kojima et al. | |
| 6,090,597 A | 7/2000 | Hirano et al. | |
| 6,461,852 B1 | 10/2002 | Tsujimoto et al. | |
| 6,841,366 B1 | 1/2005 | Bower et al. | |
| 6,878,533 B2 | 4/2005 | Tsujimoto et al. | |
| 6,984,512 B1 | 1/2006 | Liaw et al. | |
| 7,026,463 B2 | 4/2006 | Glenn et al. | |
| 7,083,942 B2 | 8/2006 | Bathe et al. | |
| 7,094,584 B2 | 8/2006 | Kreutzer et al. | |
| 7,122,369 B2 | 10/2006 | Liaw et al. | |
| 7,135,313 B2 | 11/2006 | Bathe et al. | |
| 7,211,421 B2 | 5/2007 | Tsujimoto et al. | |
| 7,256,021 B2 | 8/2007 | Hermann | |
| 2003/0049805 A1 | 3/2003 | Nagase et al. | |
| 2003/0054506 A1 | 3/2003 | Otsunna et al. | |
| 2005/0214911 A1 | 9/2005 | Marchenko et al. | |
| 2005/0250937 A9 | 11/2005 | Li et al. | |
| 2005/0260720 A1 | 11/2005 | Ito et al. | |
| 2006/0154344 A1 | 7/2006 | Van Dien et al. | |
| 2006/0154345 A1 | 7/2006 | Rayapati et al. | |

FOREIGN PATENT DOCUMENTS

| CN | ZL 20041050017.4 | 9/2008 |
| EP | 1621624 | 2/2006 |
| KR | 10-1992-0008382 | 9/1992 |

OTHER PUBLICATIONS

Anastassiadis "L-lysine fermentation" 2007, *Recent Patents on Biotechnol.*, 1(1):11-24.
Chen et al. "Organization and nucleotide sequence of the *Bacillus subtilis* diaminopimelate operon, a cluster of genes endocing the first three enzymes of diaminopimelate synthesis and dipicolinate synthase" 1993, *J. Biol. Chem.*, 268(13):9448-66.
Dobson et al. "The crystal structures of native and (S)-lysine-bound dihydrodipicolinate synthase from *Escherichia coli* with improved resolution show new features of biological significance" 2005, *Acta Cryst.*, D61:1116-24.
GenBank Accession No. L08471.
Oh et al. "Improved L-lysine production by the amplification of the *Corynebacterium glutamicum* dapA gene encoding dihydrodipicolinate synthetase in *E. coli*" 1991, *Biotech. Ltrs.*, 13(10):727-32.
Rosner "Control of lysine biosynthesis in *Bacillus subtilis*: inhibition of diaminopimelate decarboxylase by lysine" 1975, *J. Bacteriol.*, 121(1): 20-8.
Shevchenko et al. "Expression of *Bacillus subtilis* lysine biosynthesis genes in *Escherichia coli* cells" 1984, *Tsitol Genet.*, 18(1):58-60.
Vold et al. "Regulation of dihydrodipicolinate synthase and aspartate kinase in *Bacillus subtilis*" 1975, *J. Bacteriol.*, 121(3): 970-74.
Wendisch et al. "Metabolic engineering of *Escherichia coli* and *Corynebacterium gultamicum* for biotechnological production of organic acids and amino acids" 2006, *Curr. Opin. Mircobiol.*, 9:268-74 (abstract).
Yugari et al. "The condensation step in diaminopimelate synthesis" 1965, *J. Biol. Chem.*, 240(12):4710-16.

*Primary Examiner* — Suzanne M Noakes
(74) *Attorney, Agent, or Firm* — Baker Botts L.L.P.

(57) ABSTRACT

The present invention provides methods of producing L-lysine at a high yield using an *Escherichia* bacterium, especially *E. coli*, comprising a wild type or variant dapA gene of *B. subtilis*. The invention also provides related recombinant *Escherichia* bacteria, especially *E. coli*, for use to produce L-lysine.

13 Claims, No Drawings

SEQUENCE LISTING

```
<160> NUMBER OF SEQ ID NOS: 14

<210> SEQ ID NO 1
<211> LENGTH: 7016
<212> TYPE: DNA
<213> ORGANISM: Bacillus subtilis
<220> FEATURE:
<221> NAME/KEY: gene
<222> LOCATION: (5665)..(6537)
<223> OTHER INFORMATION: dapA gene

<400> SEQUENCE: 1
atcggcacag gttcgagaca tgaaacgccg gagataaacg gaatttctca cttttagag      60 cacatgttct ttaaagggac gagcacaaaa tctgcacgcg agatagcaga atcttttgat    120
cgtattggcg gccaggtcaa tgcgtttact tcaaaggaat atacctgcta ctatgcaaag    180
gtgcttgacg agcatgcgaa ttacgcgctg gacgtattag cagatatgtt ctttcattca    240
acgtttgatg aaaacgagct gaaaaaagag aaaaatgtag tatatgaaga aattaaaatg    300
tatgaagatg cgccggacga cattgtacat gatttattga gcaaagccac ttacggcaat    360
cattctttag gctacccaat tttaggaacg gaagaaacgc ttgcttcctt taacggtgac    420
tctctcagac aatacatgca tgattattat acgccggacc gagtggtgat ttcggtagcg    480
ggcaatatat ctgacagttt tatcaaagat gtagaaaaat ggttcgggtc atacgaggcg    540
aaaggcaaag cgacaggcct tgagaagcct gagttccaca cggaaaaact gacgagaaaa    600
aaagaaacag agcaggctca tttgtgcctt ggatttaaag gcttagaggt tggccatgaa    660
cgtatttatg atttaatcgt cctcaacaat gtgctcggag gcagcatgag cagccggctg    720
ttggaagatg tgcgtgaaga taaggacttt gcttattctg tttacagcta tcacagctca    780
tatgaggaca gcggaatgct aacgatttac ggcggaacgg gtgcaaatca gcttcagcag    840
ctgtcggaaa caattcaaga acccctggcc acattaaaac gtgacggcat tacctcgaaa    900
gaactggaaa acagcaaaga gcaaatgaag ggaagcttaa tgctgagctt agaaagcaca    960
aacagcaaaa tgagccgaaa cggaaaaaat caactgctgc tcggcaaaca taaaacatta   1020
gatgaaatta tcaatgaatt aaacgccgtg aacttagagc gtgttaatgg ccttgccaga   1080
caattgttta ccgaagacta tgcattagca cttatcagcc cttccggcaa tatgccgtct   1140 taaaaggaa agcctgcccc ataatggagc aggcattttt taatcccttt catcatacat   1200
agtacaaggg ggtgacagac atgcggctca gtgaattatc gggaaaggaa attgtagaca   1260
tcaaaagagc tgaacggctc ggagtgctcg gccagaccga tttggaaatc aatgaacagg   1320
atggacagat tacagcactc ctcattccca cagttaagtg gtttggtttg agaaagcaag   1380
gtcatgacat tcgtgtccca tggcaccata ttcaaaagat cggttcagat atgattatat   1440
tagatgtacc tgaggaaatg cctcctcgac aagagtaaat agcccaattg actgtgaagc   1500
gggctctaaa gaaaacatct gaaacatcgg ctgccggagc cgatgttttt ttatatggaa   1560
aaagcgcatc ttttatattc accggtatt cctttttgatc ataagatgaa ggggagctta   1620
acaactagag atccagtata tacaaagaag gtgaacgttt agaatgttaa ccggattgaa   1680
```

-continued

```
aattgcagtt atcggcggtg acgcaagaca gctcgaaatt ataagaaagc tcactgaaca    1740
gcaggctgac atctatcttg tcggttttga ccaattggat cacggtttta ccggggcagt    1800
aaaatgcaat attgatgaaa ttccttttca gcaaatagac agcatcattc ttccagtatc    1860
cgcgacaaca ggagaaggtg tcgtatcgac tgtattttcg aatgaagaag ttgtgttaaa    1920
acaggaccat cttgacagaa cgcctgcaca ttgtgtcatt ttctcaggaa tttctaacgc    1980
ctatttagaa aacattgcag ctcaggcaaa agaaaacttg ttaagctgtt ttgagcggga    2040
tgacattgcg atatacaact ctattccgac agtagaagga acgatcatgc tggctattca    2100
gcacacggat tatacgatac acggatcaca ggtggccgtt ctcggtctgg ggcgcaccgg    2160
gatgacgatt gcccgtacat ttgccgcgct cggggcgaat gtaaaagtgg gggcaagaag    2220
ttcagcgcat ctggcacgta tcactgaaat ggggctcgtt ccttttcata ccgatgagct    2280
gaaagagcat gtaaaagata tagatatttg cattaatacc ataccgagta tgattttaaa    2340
tcaaacggta ctttctagca tgacaccaaa aaccttaata ttggatctgg cctcacgtcc    2400 cggggggaacg gattttaaat atgccgagaa acaagggatt aaagcacttc ttgctcccgg    2460
gcttccaggg attgtcgctc ctaaaacagc tgggcaaatc cttgcaaacg tcttgagcaa    2520
gcttttggct gaaatacaag ctgaggaggg gaaataagga tgtcgtcatt aaaaggaaaa    2580
agaatcgggt ttgggctgac cgggtcgcat tgcacatatg aagcggtttt cccgcaaatt    2640
gaggagttgg tcaacgaagg agctgaagtc cgtccggttg tcacatttaa tgtaaaatct    2700
acaaataccc gatttggaga gggcgcagaa tgggttaaaa aaattgaaga cctgactgga    2760
tatgaggcca ttgattcgat tgtaaaggca gaacctcttg ggccgaagct gccccttgac    2820
tgcatggtca ttgcgccttt aacaggcaat tcaatgagca agctggcaaa tgccatgacg    2880
gacagcccgg tgctgatggc ggcaaaagcg acaatccgga acaatcggcc tgtcgttctg    2940
ggtatctcga caaatgatgc tcttggttta acggaacaa atttaatgag gctcatgtca    3000
acaaaaaata tctttttttat tccattcggg caagatgatc catttaaaaa accgaattca    3060
atggtagcca aaatggatct gcttccgcaa acgattgaaa aggcactcat gcaccagcag    3120
cttcagccga ttctagttga gaattatcag ggaaatgact aaatttacag aaaatctttc    3180
ccaaactaaa aaattcggtc atcacccgca tattctatgg taaaataaaa cgtaaaatca    3240
tagtcaaatc aattcaatga agctgattgg cggaaggagt tttacagatg ggaagaggtt    3300
tacacgtagc tgttgtcgga gcgacagggg ctgtgggaca acaaatgctt aaaacacttg    3360
aagacagaaa ctttgaaatg gacacactta cattgctatc ttcaaaacgc tctgcgggga    3420
caaaagtcac gtttaaggc caagagctga ctgttcagga agcttctcct gagagctttg    3480 aagggggtaaa tattgctttg ttcagcgccg gcggaagcgt atcacaagca ttggcaccag    3540
aagctgtaaa acgcggcgct attgttatag ataatacgag tgcgttccgc atggatgaaa    3600
atacaccgct tgttgtgcca gaagtgaatg aggcagactt gcatgaacac aacggcatta    3660
ttgccaatcc aaactgctct acaatccaaa tggttgcggc acttgaaccg atccgcaaag    3720
catatggctt aaacaaggtc atcgtatcaa cttaccaggc agtatcagga gcgggtaatg    3780
aagctgtaaa agagctttac agccaaacac aggcgatttt aaataaagaa gaaatagagc    3840
ctgagatcat gcctgtaaaa ggtgacaaaa aacactatca aatcgccttc aacgcgattc    3900
cgcaaatcga taaattccaa gataacggct atacgtttga ggaaatgaaa atgataaatg    3960
aaacgaaaaa aatcatgcac atgcctgacc ttcaagtagc ggctacatgt gtgagactgc    4020
caatccaaac tgggcactca gagtccgtct acatcgaaat agaccgtgat gacgctacag    4080
```

```
ttgaagatat taaaaatcta ttgaaagaag ctccgggcgt gacacttcag gatgatccaa    4140
gccagcagct ttatccgatg cctgctgatg ctgtcggcaa aaacgatgtg tttgtaggcc    4200
gcatccgcaa agacttggac agagcaaacg gttttcattt atgggttgtt tctgataacc    4260
tattaaaagg cgcggcatgg aactctgttc aaattgcaga aagcctgaaa aaactaaacc    4320
tcgtataaaa gagagaattt tctaaagacg aatagaagag agtaaggcgc tatcagcctg    4380
ctctcttctg ttacgtccga ataatttgga gtgaaaacag tgaagataat tgttcaaaag    4440
ttcggcggaa catcagtaaa agatgataaa ggccgcaaac tggctttagg gcatattaaa    4500
gaagcaatca gtgaaggata taaggttgtc gttgtcgttt cagcgatggg ccgaaaaggg    4560
gacccgtatg caacagattc tttgctcggg ctgctttacg gcgatcagtc agcgatttct    4620
cctagggagc aggatttgct tttatcttgc ggagagacta tttcctctgt cgtctttaca    4680
agcatgctgc ttgataacgg tgtgaaagca gctgcgctga caggggctca ggctggcttt    4740
ttaacgaatg atcagcatac taatgcgaaa atcattgaaa tgaaaccgga gcgtttattc    4800
agtgtgctcg ccaatcatga tgcggtagtc gtcgcaggct tccagggcgc aactgaaaag    4860
ggtgatacaa caacaatcgg cagaggggc agcgatacgt ctgcagccgc actcggagca    4920
gctgttgatg cggaatacat cgatattttc accgatgtag aaggcgtgat gactgctgac    4980
ccaagagtgg tagaaaatgc aaaaccgctt cctgttgtga cgtatacgga aatctgcaac    5040
ctggcgtatc agggggccaa ggtcatttct ccgcgtgctg tggaaatcgc aatgcaggcc    5100
aaggttccga tccgcgtccg ttcgacttat tcgaatgata aaggcacatt ggtgacatca    5160
catcactctt ccaaggtcgg cagtgatgtt tttgaaaggc tgattacggg aatcgcccat    5220
gtcaaagatg tcacgcagtt caaagtgcct gcgaaaatcg gccagtataa cgttcagact    5280
gaagtgttca aggctatggc aaaacgctgga atcagtgtcg atttctttaa cattacacct    5340
agtgaaatcg tctatacggt agccggaaat aaaacagaaa cagctcagcg tatttttaatg    5400
gatatgggct atgatccaat ggtgacgaga aactgcgcga aggtatcggc ggtcggcgcg    5460
ggcattatgg gtgttcccgg tgttacgtcc aaaattgtat cggctctttc agaaaaagaa    5520
attccgatcc ttcagtcggc tgacagccat acgacgatat gggtgctcgt ccatgaagcg    5580
gatatggttc ctgctgtaaa cgctttgcat gaagtgtttg aactttcgaa gtaaatgtga    5640
ttgaatcatg atgaggtgaa taaaatgaat ttcggaaatg tgtctacagc gatgattaca    5700
cccctttgaca ataaagggaa cgtagacttt caaaaactgt ctacactgat tgattacttg    5760
ttgaaaaacg gaacggattc tttagtagta gcgggaacaa ctggagaatc tccgaccctt    5820
tcaactgaag aaaaaattgc gcttttttgaa tatacggtaa agaagtaaa cggacgggtg    5880
cccgttatcg ctggtactgg gagcaacaac acgaaagatt ccattaagct gacaaaaaaa    5940
gctgaggaag cgggcgtgga cgctgttatg cttgttaccc cgtattacaa taaaccttct    6000
caagaaggaa tgtaccagca tttttaaagca attgcggcag agacatctct tccggttatg    6060
ctctataatg ttcctggccg tacggttgct tctcttgctc ctgaaacgac gatccgtttg    6120
gcggcagaca ttccgaatgt ggttgcgatt aaagaagcga gcggagacct cgaagcgatt    6180
acaaaaatta ttgctgaaac acctgaagac ttctatgtct attcagggga tgatgctcta    6240
acgcttccaa ttctttcagt tggaggtaga ggagttgtgt cagtggcgag ccatattgca    6300
ggcactgata tgcagcaaat gatcaaaaat tatacgaatg ggcaaacagc taatgcggca    6360
ctgattcatc agaaactgct gccgattatg aaggaactgt ttaaagcgcc taatcctgct    6420
ccagtcaaaa cagcgcttca gctgagaggt cttgatgtcg gttctgtgcg tctgcctcta    6480
```

```
gtcccattaa ctgaggatga acgtctgagc ttaagcagca cgatcagcga actgtaagaa    6540
aatttcatac agtgaaacaa acgcggtcat tctcacattc agctgagttt gaccgtttct    6600
tttacatatt ggttttccct aaaccttctg ctttatcttg ttttctaaat ttactttcag    6660
ttataatagg aacaagtgat gatggacggg tatgagacta ggaggatata gattttgaaa    6720
aagaaaaata cagaaaacgt tagaattatc gcccttggcg gtgtcggaga gatcgggaat    6780
taccattttt ggacagctgt cttttcagca gcagccatta tgctcggggg ctttctcgct    6840 gacttttttca cagtgcaaat gattttttat gcaagctcta ttctatattt tttgagtgga    6900
ttgatgatga tgaaaacagg ctgacgcggt cagcctgttt ttttatgcgg ctgaaatgcg    6960
gcaccgcatc aacgttttttg tgctggagtc gtgctgattt tttttgagcg gaattc       7016
```

<210> SEQ ID NO 2
<211> LENGTH: 290
<212> TYPE: PRT
<213> ORGANISM: Bacillus subtilis

<400> SEQUENCE: 2

```
Met Asn Phe Gly Asn Val Ser Thr Ala Met Ile Thr Pro Phe Asp Asn
1               5                   10                  15

Lys Gly Asn Val Asp Phe Gln Lys Leu Ser Thr Leu Ile Asp Tyr Leu
                20                  25                  30

Leu Lys Asn Gly Thr Asp Ser Leu Val Val Ala Gly Thr Gly Glu
            35                  40                  45

Ser Pro Thr Leu Ser Thr Glu Glu Lys Ile Ala Leu Phe Glu Tyr Thr
        50                  55                  60

Val Lys Glu Val Asn Gly Arg Val Pro Val Ile Ala Gly Thr Gly Ser
65                  70                  75                  80

Asn Asn Thr Lys Asp Ser Ile Lys Leu Thr Lys Lys Ala Glu Glu Ala
                85                  90                  95

Gly Val Asp Ala Val Met Leu Val Thr Pro Tyr Tyr Asn Lys Pro Ser
            100                 105                 110

Gln Glu Gly Met Tyr Gln His Phe Lys Ala Ile Ala Ala Glu Thr Ser
        115                 120                 125

Leu Pro Val Met Leu Tyr Asn Val Pro Gly Arg Thr Val Ala Ser Leu
    130                 135                 140

Ala Pro Glu Thr Thr Ile Arg Leu Ala Ala Asp Ile Pro Asn Val Val
145                 150                 155                 160

Ala Ile Lys Glu Ala Ser Gly Asp Leu Glu Ala Ile Thr Lys Ile Ile
                165                 170                 175

Ala Glu Thr Pro Glu Asp Phe Tyr Val Tyr Ser Gly Asp Asp Ala Leu
            180                 185                 190

Thr Leu Pro Ile Leu Ser Val Gly Gly Arg Gly Val Val Ser Val Ala
        195                 200                 205

Ser His Ile Ala Gly Thr Asp Met Gln Gln Met Ile Lys Asn Tyr Thr
    210                 215                 220

Asn Gly Gln Thr Ala Asn Ala Ala Leu Ile His Gln Lys Leu Leu Pro
225                 230                 235                 240

Ile Met Lys Glu Leu Phe Lys Ala Pro Asn Pro Ala Pro Val Lys Thr
                245                 250                 255

Ala Leu Gln Leu Arg Gly Leu Asp Val Gly Ser Val Arg Leu Pro Leu
            260                 265                 270

Val Pro Leu Thr Glu Asp Glu Arg Leu Ser Leu Ser Thr Ile Ser
        275                 280                 285
```

Glu Leu
    290

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(21)
<223> OTHER INFORMATION: DapA-F primer

<400> SEQUENCE: 3
cggcgatcgt ttctgttggc a                                                21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(21)
<223> OTHER INFORMATION: DapA-R primer

<400> SEQUENCE: 4
atctgggcca tatcacgcgc t                                                21

<210> SEQ ID NO 5
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(45)
<223> OTHER INFORMATION: bsdapa119muts primer

<400> SEQUENCE: 5
tcaagaagga atgtaccagt atttcaaagc aattgcggca gagac                      45

<210> SEQ ID NO 6
<211> LENGTH: 45
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(45)
<223> OTHER INFORMATION: bsdapa119mutas primer

<400> SEQUENCE: 6
gtctctgccg caattgcttt gaaatactgg tacattcctt cttga                      45

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(27)
<223> OTHER INFORMATION: ptrcBSdapA1-F primer

<400> SEQUENCE: 7

```
ggacactgtc taatgtgagt tagcgcg                                               27
```

<210> SEQ ID NO 8
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(27)
<223> OTHER INFORMATION: ptrcBSdapA1-R primer

<400> SEQUENCE: 8

```
cactagtatt gaagcattta tcagggt                                               27
```

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(18)
<223> OTHER INFORMATION: ptrcBSdapA2-F primer

<400> SEQUENCE: 9

```
gcggccgctg tgcaggtc                                                         18
```

<210> SEQ ID NO 10
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(26)
<223> OTHER INFORMATION: ptrcBSdapA2-R primer

<400> SEQUENCE: 10

```
gaccactgtc agggttattg tctcat                                                26
```

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(23)
<223> OTHER INFORMATION: LDCup primer

<400> SEQUENCE: 11

```
atgaacatca ttgccattat ggg                                                   23
```

<210> SEQ ID NO 12
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(23)
<223> OTHER INFORMATION: f1DN primer

<400> SEQUENCE: 12

```
ttactgctca tacagttcca acg                                                  23

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(20)
<223> OTHER INFORMATION: FRT5 primer

<400> SEQUENCE: 13
attccgggga tccgtcgacc                                                      20

<210> SEQ ID NO 14
<211> LENGTH: 59
<212> TYPE: DNA
<213> ORGANISM: Artificial sequence
<220> FEATURE:
<223> OTHER INFORMATION: Synthetic oligonucleotide
<220> FEATURE:
<221> NAME/KEY: Unsure
<222> LOCATION: (1)..(59)
<223> OTHER INFORMATION: HPA1FRT3 primer

<400> SEQUENCE: 14
aacagcacgt tactcgcccg gaagccgctc tggcaagtta tgtaggctgg agctgcttc          59
```

RECOMBINANT MICROORGANISM AND METHOD FOR PRODUCING L-LYSINE

CROSS-REFERENCE TO RELATED APPLICATIONS

The present application claims priority to U.S. Provisional Application Ser. No. 61/033,099, filed Mar. 3, 2008, the entirety of the disclosure of which is explicitly incorporated by reference herein.

SEQUENCE LISTING

The specification further incorporates by reference the Sequence Listing submitted herewith. Pursuant to 37 C.F.R. §1.52(e)(5), the Sequence Listing text file, identified as 0786680106seqlist.txt, is 15,349 bytes and was created on Feb. 26, 2009.

FIELD OF THE INVENTION

The present invention pertains to the field of biotechnology. In particular, the invention provides methods for producing L-lysine by growing a transformed *Escherichia* bacterium, especially *E. coli*, which comprises a wild type or variant *Bacillus subtilis* dapA gene.

BACKGROUND OF THE INVENTION

L-lysine is an essential amino acid that is not synthesized in animals. Many wild type and mutant bacterial strains have been found to produce L-lysine. Being widely used as a feed additive, medicament, chemical agent and food ingredient, L-lysine has been produced by large-scale fermentation using mainly a *Coryneform* bacterium or an *Escherichia* bacterium.

In most bacteria, L-lysine is naturally synthesized from aspartate in a nine-step enzymatic pathway, including two steps shared by the biosynthesis pathways of methionine and threonine (Anastassiadis, S., Recent patents on Biotechnology 2007, 1(1):11-24; Chen, N. et al., *J. Biol. Chem.* 1993, 268(13):9448-66). The regulatory mechanism of lysine biosynthesis is complex and varies widely in different bacterial species (Chen, N. et al., *J. Biol. Chem.* 1993, 268(13):9448-66). For example, dihydrodipicolinate synthase ("DDPS"), an enzyme that catalyzes the first step into the lysine biosynthesis branch, suffers feedback inhibition by L-lysine in Gram-negative bacteria (e.g., *E. coli*, *Bacillus sphaericus* and *Methanobacterium thermoautotrophicum*), but not in Gram-positive bacteria (e.g., *Bacillus licheniformis, Bacillus megaterium, Bacillus subtilis, Corynebacterium glutamicum, Bacillus cereus*, and *Bacillus lactofermentum*) (Dobson, R. et al., *Acta Cryst.* 2005, D61:1116-24). Further, the regulation of the lysine biosynthesis pathway in *Bacillus subtilis* ("*B. subtilis*") is unique because it involves a dual control by lysine and one of its precursors, diaminopimelate (Chen, N. et al., *J. Biol. Chem.* 1993, 268(13):9448-66).

Consistent with the diverse sensitivity to feedback inhibition of DDPS by L-lysine, limited homology in the DDPS protein sequence and in its corresponding gene, dapA, is observed among bacterial strains from different genera. DDPS in *B. subtilis* has an amino acid sequence about 43% and 40% identical to those in *E. coli* and *Corynebacterium Glutamicum* ("*C. Glutamicum*"), respectively (Chen, N. et al., *J. Biol. Chem.* 1993, 268(13):9448-66). Even in the same bacterial genus, different bacterial strains exhibit only modest homology. For example, the dapA gene in *Bacillus methanolicus* ("*B. methanolicus*") is about 65% identical in nucleotide or amino acid sequence to a previously known dapA gene in *B. subtilis* (U.S. Pat. No. 6,878,533).

One way to improve L-lysine production by an *Escherichia* bacterium is to overcome the feedback inhibition of DDPS by L-lysine. Mutations have been made in the wild type dapA gene of an *Escherichia* bacterium to desensitize DDPS to L-lysine (U.S. Pat. No. 6,040,160). Attempts have also been made to introduce a wild type dapA gene of a non-*Escherichia* bacterium, in which the corresponding DDPS does not suffer feedback inhibition by L-lysine, into an *Escherichia* bacterium, but have failed to produce consistent and satisfactory results.

A Korean group reported that an introduction of a wild type dapA gene from a lysine overproducing *C. glutamicum* strain into a lysine producing mutant *E. coli* strain (TF1) led to a parallel increase of a lysine-sensitive DDPS activity and lysine production (Oh, J. et al., *Biotech. Ltrs.* 1991, 13(10): 727-32; Korean Pat. Pub. No. 10-1992-0008382). However, expression of the same wild type dapA gene in two other *E. coli* strains (TF13 and TF23) failed to result in a high yield of lysine production. The fact that the regulatory mechanism involved in lysine biosynthesis is more complex in *E. coli* than in *Coryneform* bacteria was cited for the inconsistent results.

Expression of a foreign dapA gene is challenging because the corresponding foreign DDPS protein is likely subject to decomposition by protease and formation of an insoluble inclusion body in an *Escherichia* bacterium (U.S. Pat. No. 6,040,160). In addition, a DDPS of *C. glutamicum* (Oh, J. et al., *Biotech. Ltrs.*, 1991, 13(10):727-32; Korean Pat. Pub. No. 10-1992-0008382) or *B. methanolicus* (U.S. Pat. No. 6,878, 533) is not expected to exhibit its advantageous activity, i.e., a lysine-insensitive DDPS activity that leads to a high yield of lysine production, in *E. coli* partly because the optimal cultivation temperature for *C. Glutamicum* or *B. methanolicus* deviates from that for *E. coli* by about ten or more degrees.

An extremely complicated regulation of lysine synthesis was observed in *E. coli* cells, in which genes involved in lysine biosynthesis in *B. subtilis* were expressed (Shevchenko, T. N. et al., *Tsitol Genet.* 1984, 18(1):58-60). In particular, the expression of these foreign genes, including a foreign dapA gene, in *E. coli* cells failed to increase lysine production to a high and satisfactory level. It was suggested that a considerable increase in lysine biosynthesis be achieved by using an *E. coli* or *B. subtilis* strain having mutations in its natural genes involved in lysine biosynthesis to desensitize feedback inhibition by lysine and diaminopimelate.

At present, there has not been any effective method for producing L-lysine using an *Escherichia* bacterium comprising a wild type or variant *B. subtilis* dapA gene. As the demand of L-lysine, especially for animal feed, continuously increases along with the global population expansion, there is a need to develop novel and effective methods for improving L-lysine production using an *Escherichia* bacterial strain.

SUMMARY OF THE INVENTION

In accordance of the present invention, an introduction of a wild type or variant dapA gene of *B. subtilis* into an *Escherichia* bacterium improves L-lysine production by the *Escherichia* bacterium to industrial levels. Further, the transformed *Escherichia* bacterium may be used to produce L-lysine in a cultivation medium at a high yield (e.g., at least 25, 50, 75, 100, 125 or 150 grams per liter).

The present invention provides a recombinant DNA autonomously replicable in an *Escherichia* bacterium and comprising a wild type or variant dapA gene of *B. subtilis*. A variant *B. subtilis* dapA gene has a non-identical but substantially (e.g., 90%, 95%, or 99%) identical sequence to that of a wild type *B. subtilis* dapA gene. The recombinant DNA may be used to introduce a *B. subtilis* dapA gene into an *Escherichia* bacterium to increase L-lysine production.

The *B. subtilis* dapA gene may have a nucleic acid sequence identical or substantially (e.g., 90%, 95%, or 99%) identical to that of a *B. subtilis* dapA gene as set forth in GenBank Accession No. L08471 (bases 5665-6537 of SEQ ID NO: 1) and Chen, N. et al., *J. Biol. Chem.* 1993, 268(13): 9448-66). A variant *B. subtilis* dapA gene may comprise one or more nucleotide modifications in SEQ ID NO: 1. In one specific non-limiting embodiment, a variant *B. subtilis* dapA gene comprises two mutations from C to T at nucleotide residue 6019 and from T to C at nucleotide residue 6024 of SEQ ID NO: 1.

Further, the *B. subtilis* dapA gene may encode a protein having an amino acid sequence identical or substantially (e.g., 90%, 95%, or 99%) identical to the deduced amino acid sequence of the *B. subtilis* dapA gene as set forth in GenBank Accession No. L08471 (SEQ ID NO: 2) and Chen, N. et al., *J. Biol. Chem.* 1993, 268(13):9448-66). The protein may have an amino acid sequence comprising one or more amino acid modifications in SEQ ID NO: 2. In one specific non-limiting embodiment, a variant *B. subtilis* dapA gene encodes a protein having an amino acid sequence comprising a mutation from histidine to tyrosine at amino acid residue 119 of SEQ ID NO: 2 ("H119Y variant"). The *B. subtilis* dapA gene may encode a protein having a DDPS activity.

The present invention also provides an *Escherichia* bacterium comprising a wild type or variant *B. subtilis* dapA gene for producing L-lysine in a cultivation medium. The *Escherichia* bacterium may produce L-lysine at least 50 grams per liter in the cultivation medium. In one specific non-limiting embodiment, an *Escherichia* bacterium comprising a wild type *B. subtilis* dapA gene is provided for producing L-lysine. In another specific non-limiting embodiment, an *Escherichia* bacterium comprising a H119Y variant *B. subtilis* dapA gene is provided for producing L-lysine.

The present invention further provides methods for producing L-lysine by growing an *Escherichia* bacterium in a cultivation medium and collecting L-lysine from the cultivation medium, wherein the bacterium comprises a wild type or variant *B. subtilis* dapA gene. L-lysine is allowed to accumulate before being harvested or collected from the cultivation medium. L-lysine may be collected from the cultivation medium when L-lysine reaches at least 25, 50, 75, 100, 125 or 150 grams per liter, preferably at least 50 grams per liter. In one specific non-limiting embodiment, an *Escherichia* bacterium comprising a wild type *B. subtilis* dapA gene is grown in a cultivation medium, and L-lysine is collected from the cultivation medium. In another specific non-limiting embodiment, an *Escherichia* bacterium comprising a H119Y variant *B. subtilis* dapA gene is grown in a cultivation medium, and L-lysine is collected from the cultivation medium.

DETAILED DESCRIPTION OF THE INVENTION

The present invention advantageously provides methods, transformed bacteria belonging to the genus of *Escherichia* and recombinant DNAs for producing L-lysine by fermentation. It has now been discovered that L-lysine can be produced at a high yield by an *Escherichia* bacterium comprising a wild type or variant dapA gene of *B. subtilis*.

For clarity of description, and not by way of limitation, the invention is explained in details in the following subsections:
(1) a recombinant DNA;
(2) a transformed *Escherichia* bacterium; and
(3) a method for producing L-lysine.

(1) A Recombinant DNA

The recombinant DNA of the present invention carries a wild type or variant dapA gene of a *B. subtilis* strain, and replicates autonomously in an *Escherichia* bacterial strain. It may be obtained by inserting a DNA fragment comprising the *B. subtilis* dapA gene into an expression vector replicable in an *Escherichia* bacterial strain.

In the *B. subtilis* strain, the dapA gene is expressed and the corresponding DDPS does not suffer substantial (e.g., 10%, 20%, 30%, 40%, 50%, 60%, or more) feedback inhibition by L-lysine. The *B. subtilis* strain may or may not be a L-lysine producer. A preferred *B. subtilis* strain is W168, which is not a lysine producer. This strain is available from *Bacillus* Genetic Stock Center, Ohio State University, U.S.A.

A DNA fragment comprising a wild type *B. subtilis* dapA gene ("BsdapA gene") can be obtained from the chromosomal DNA of a wild type *B. subtilis* strain. The chromosomal DNA can be prepared from a *B. subtilis* strain using standard techniques known in the art. The DNA fragment can be obtained by amplifying the wild type *B. subtilis* dapA gene from the chromosomal DNA using a polymerase chain reaction method (PCR). Suitable PCR primers can be prepared based on the previously published dapA gene sequence in *B. subtilis* or other bacterial strains (e.g., *E. coli* and *C. glutamicum*) (Chen, N. et al., *J. Biol. Chem.* 1993, 268(13): 9448-66). For example, a pair of single-stranded 21-mer primers, DapA-F (SEQ ID NO: 3) and DapA-R (SEQ ID NO: 4), may be used.

The nucleic acid sequences of SEQ ID NOS: 3 and 4 are shown below:

```
                                         SEQ ID NO: 3
(DapA-F) CGGCGATCGTTTCTGTTGGCA

SEQ ID NO: 4
(DapA-R) ATCTGGGCCATATCACGCGCT
```

A DNA fragment comprising a variant *B. subtilis* dapA gene can be similarly obtained from the chromosomal DNA of a *B. subtilis* strain mutated in vivo. A variant *B. subtilis* dapA gene can also be obtained by introducing modifications into the wild type *B. subtilis* dapA gene in vitro by standard techniques known in the art, such as site-directed mutagenesis and PCR-mediated mutagenesis.

The sequence of the resulting DNA fragment can be determined by a commonly known method using suitable primers (e.g., DapA-F and DapA-R).

The *B. subtilis* dapA gene may have a nucleic acid sequence identical or substantially (e.g., 90%, 95%, or 99%) identical to that of the *B. subtilis* dapA gene as set forth in GenBank Accession No. L08471 (bases 5665-6537 of SEQ ID NO: 1) and Chen, N. et al., *J. Biol. Chem.* 1993, 268(13): 9448-66). A wild type *B. subtilis* dapA gene may have a nucleic acid sequence identical to SEQ ID NO: 1. A variant *B. subtilis* dapA gene may comprise one or more nucleotide modifications in SEQ ID NO: 1. For example, a variant *B. subtilis* dapA gene may comprise two mutations from C to T at nucleotide residue 6019 and from T to C at nucleotide residue 6024 of SEQ ID NO: 1. The sequence percentage identity may be determined by standard software such as BLAST or FASTA.

Further, the *B. subtilis* dapA gene may encode a protein having an amino acid sequence identical or substantially (e.g., 90%, 95%, or 99%) identical to the deduced amino acid sequence of the *B. subtilis* dapA gene as set forth in GenBank Accession No. L08471 (SEQ ID NO: 2) and Chen, N. et al., *J. Biol. Chem.* 1993, 268(13):9448-66). A wild type *B. subtilis* dapA gene may encode a protein having an amino acid sequence identical to SEQ ID NO: 2. A *B. subtilis* dapA gene may also encode a protein having an amino acid sequence comprising one or more amino acid modifications in SEQ ID NO: 2. For example, a variant *B. subtilis* dapA gene may encode a protein having an amino acid sequence comprising a mutation from histidine to tyrosine at amino acid residue 119 of SEQ ID NO: 2 ("H119Y variant").

The amino acid modifications include amino acid substitutions, additions and deletions. Modifications can be introduced by standard techniques known in the art, such as site-directed mutagenesis and PCR-mediated mutagenesis. Amino acid substitutions may include those in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The amino acid substitutions may also include those that correlate with the amino acid substitutions in the wild type dapA gene of an *Escherichia* bacterium known to desensitize the corresponding DDPS to L-lysine.

The DNA fragment comprising a wild type or variant dapA gene of *B. subtilis* can be subsequently ligated with a suitable expression vector to produce a recombinant DNA comprising the dapA gene. A suitable DNA expression vector replicates autonomously in an *Escherichia* bacterial strain, and comprises a selectable genetic marker. A selectable genetic marker can detect resistance to an antibiotic (e.g., ampicillin, tetracycline, kanamycin and neomycin), a color change or any other characteristics that can distinguish transformed hosts from untransformed hosts. Examples of suitable vectors include an *E. coli* expression vector such as pTrc99A, pUC19, pUC18, pBR322, pHSG299, pHSG399, pHSG398, RSF1010, pMW119, pMW118, pMW219, pMW218 and pSTV28. It is preferable that the DNA fragment is inserted into a DNA expression vector in a way such that the dapA gene is under the control of a strong promoter of *E. coli*. Examples of suitable promoters include trc, tac, lac and T7, preferably trc.

The *B. subtilis* dapA gene may encode a protein having a DDPS activity. The presence of a recombinant DNA comprising a *B. subtilis* dapA gene may be confirmed by an elevated level of DDPS activity in a bacterial strain transformed with the recombinant DNA or recovery of auxotrophy in a DDPS deficient bacterial strain (e.g., *E. coli* JE7627 strain) transformed with the recombinant DNA.

(2) A Transformed *Escherichia* Bacterium

An *Escherichia* bacterium may be transformed with a recombinant DNA comprising a wild type or variant dapA gene of *B. subtilis* using standard techniques known in the art. The parent (untransformed) *Escherichia* bacterium may carry a wild type or mutant natural dapA gene, and express a corresponding wild type or mutant natural DDPS. The enzymatic activity of the natural DDPS may suffer feedback inhibition by L-lysine. The parent *Escherichia* bacterium may be a L-lysine producer. The activity of another natural enzyme involved in lysine biosynthesis may be enhanced. For example, an *E. coli* strain comprising a DNA coding for a natural aspartokinase III having a mutation to desensitize feedback inhibition by L-lysine (U.S. Pat. No. 6,040,160) can be used. It is preferred that the *Escherichia* bacterial strain is *E. coli*. It is further preferred that the *Escherichia* bacterium is an *E. coli* strain that is commonly used for industrial production of L-lysine.

After transformation, the *Escherichia* bacterium harbors a wild type or variant dapA gene of *B. subtilis*. The presence of a *B. subtilis* dapA gene in the transformed bacterium can be determined by standard techniques known in the art. The *B. subtilis* dapA gene can be carried on a plasmid. It may also be integrated into a chromosome of the transformed *Escherichia* bacterium. The transformed *Escherichia* bacterium produces L-lysine at a high yield (e.g., at least 25, 50, 75, 100, 125 or 150 grams per liter).

In one embodiment, an *E. coli* strain B-3996 (available at Research Institute for Genetics and Industrial Microorganism Breeding under Reg. No. RIA 1867) is transformed with a recombinant DNA comprising a wild type dapA gene (e.g., pTrc99A-BsdapA) after kicking out the sole plasmid pVIC40 (U.S. Pat. No. 6,040,160) to make a transformed bacterial strain B-399/pTrc99A-BsdapA. A control strain B-399/pTrc99A is similarly prepared by transformation with a corresponding recombinant DNA without BsdapA (e.g., pTrc99A). The cultivation medium is prepared by mixing a sterilized solution (containing 16 g/L $(NH_4)_2SO_4$, 1 g/L $KH_2PO_4$, 1 g/L $MgSO_4.7H_2O$, 0.01 g/L $FeSO_4.7H_2O$, 0.01 g/L $MnSO_4.5H_2O$, 2 g/L yeast extract (Difco), 0.5 g/L L-methionine, 0.1 g/L L-threonine, and 0.05 g/L L-isoleucine at pH 7.0) with sterilized 20% glucose at a ratio of 4 to 1. Glucose can be fed to improve L-lysine production. Sterilized pharmacopoeial $CaCO_3$ is subsequently added to the mixture and dissolved to a final concentration of 30 g/L. Appropriate antibiotics (e.g., 15 µg/ml tetracycline, and 5 kanamycin) can also be added. Both strains are cultivated at an agitation of 114-116 rpm and at 37° C. for 48 hours. L-lysine is harvested and analyzed from the culture medium. It is expected that bacterial strain B-399/pTrc99A-BsdapA will produce L-lysine of at least 10 grams per liter, which will be significantly more than the control strain B-399/pTrc99A.

In another embodiment, an *E. coli* bacterial strain DC037 from Global Bio-Chem Technology Group Company Limited was used to prepare a recombinant *E. coli* comprising a wild type dapA gene of *B. subtilis* (DC051), a recombinant *E. coli* comprising a H119Y variant dapA gene of *B. subtilis* (DC231), and a recombinant *E. coli* control (DC073), which produced L-lysine at 150, 180 and 20 grams per liter, respectively. The preparation and testing of these recombinant *E. coli* strains are described in Examples 3 and 4.

Bacteria of strains DC051 and DC231 were deposited on Feb. 26, 2009 with the China General Microbiological Culture Collection Center (CGMCC), Institute of Microbiology, Chinese Academy of Sciences, Beijing 100080, PR China, under the Budapest Treaty on the International Recognition of the Deposit of Microorganisms for the Purposes of Patent Procedure, and were given accession numbers of CGMCC No. 2923 and CGMCC No. 2924, respectively.

The DDPS activity in the transformed *Escherichia* bacterium may not suffer substantial (e.g., 10%, 20%, 30%, 40%, 50%, 60%, or more) feedback inhibition by L-lysine. The DDPS activity of the transformed *Escherichia* bacterium may be reduced no more than 50% in the presence of 10 mM L-lysine.

The DDPS activity in a bacterium can be measured in accordance with the method described by Yugari, Y. and Gilvarg C. in *J. Biol. Chem.*, 1965, 240(12):4710-16, or any other suitable method. For example, a bacterial extract is added to a reaction solution containing 50 mM imidazole-HCl (pH 7.4), 20 mM L-aspartic semialdehyde and 20 mM sodium pyruvate, and incubated at 37° C. for 10 minutes. A reaction solution without sodium pyruvate can be used as a blank. The DDPS activity is measured by the amount of dihydrodipicolinate generated by the reaction, which is detected by a spectrophotometer at a wavelength of 270 nm. Various amounts of L-lysine are added to the reaction mixture to evaluate lysine sensitivity of the DDPS activity.

(3) A Method for Producing L-lysine

L-lysine can be produced by growing an *Escherichia* bacterium comprising a wild type or variant *B. subtilis* dapA gene in a cultivation medium. A medium suitable for optimal growth of an *Escherichia* bacterium is desirable (Anastassiadis, S., *Recent Patents On Biotechnology* 2007, 1(1):11-24). An antibiotic (e.g., ampicillin) is desirable in the medium to keep selectivity and stability of the transformed *Escherichia* bacterium.

For example, the cultivation medium is prepared by mixing a sterilized solution (containing 16 g/L $(NH_4)_2SO_4$, 1 g/L $KH_2PO_4$, 1 g/L $MgSO_4.7H_2O$, 0.01 g/L $FeSO_4.7H_2O$, 0.01 g/L $MnSO_4.5H_2O$, 2 g/L yeast extract (Difco), 0.5 g/L L-methionine, 0.1 g/L L-threonine, and 0.05 g/L L-isoleucine at pH 7.0) with sterilized 20% glucose at a ratio of 4 to 1. Glucose can be fed to improve L-lysine production. Sterilized pharmacopoeial $CaCO_3$ is subsequently added to the mixture and dissolved to a final concentration of 30 g/L. Appropriate antibiotics (e.g., 15 µg/ml tetracycline, and 5 µg/ml kanamycin) can also be added.

The cultivation conditions optimal for an *Escherichia* bacterium are desirable (Anastassiadis, S., *Recent Patents On Biotechnology* 2007, 1(1):11-24). Cultivation is preferably carried out under an aerobic condition at a temperature between 25° C. and 45° C. and a pH between 5 and 8. The concentration of L-lysine reaches a maximum after cultivation for about 2 to 10 days. The bacterial growth can be monitored based on cell density of the culture medium measured by a spectrophotometer.

L-lysine is allowed to accumulate in the cultivation medium of a transformed *Escherichia* bacterium cultivated according to the present invention. L-lysine can be harvested by various methods (e.g., ion-exchange chromatographic methods) to produce L-lysine-HCl before or after cell separation by centrifugation and filtration of the cultivation medium; or L-lysine broth can be harvested to produce L-lysine sulphate by a pelletizing process (Anastassiadis, S., *Recent Patents On Biotechnology* 2007, 1(1):11-24; Chinese Pat. No. 200410050017.4). L-lysine may be harvested or collected from the cultivation medium when L-lysine reaches at least 5 to 10 grams per liter, or at least 25, 50, 75, 100, 125 or 150 grams per liter in a large-scale fermentation process, preferably at least 50 grams per liter. The amount of L-lysine can be determined by various analytical methods known in the art (e.g., HPLC).

EXAMPLES

The invention now being generally described, it will be more readily understood by reference to the following examples, which are included merely for purposes of illustration of certain aspects and embodiments of the present invention, and are not intended to limit the invention.

Example 1

Construction of Plasmid pTrc99A-BsdapA

Plasmid pTrc99A-BsdapA was constructed to comprise a wild type *B. subtilis* dapA gene. The chromosomal DNA was prepared from a wild type *B. subtilis* strain W168 (Bacillus Genetic Stock Center, Ohio State University, U.S.A.) using a commonly known method. A DNA fragment of 0.88 kb was obtained by amplifying the wild type dapA gene in the chromosomal DNA using a pair of primers, DapA-F (SEQ ID NO: 3) and DapA-R (SEQ ID NO: 4), having nucleic acid sequences shown in SEQ ID NOS: 3 and 4, respectively. The DNA fragment was recovered, digested with restriction enzymes EcoRI and HindIII, and ligated with a pTrc99A plasmid previously digested with the same restriction enzymes to produce a pTrc99A-BsdapA plasmid. Plasmid pTrc99A-BsdapA comprised a nucleic acid sequence of SEQ ID NO: 1. The nucleic acid sequence encodes a protein having an amino acid sequence of SEQ ID NO: 2.

Example 2

Construction of Plasmid pTrc99A-BsdapAH119Y

Plasmid pTrc99A-BsdapAH119Y was constructed to comprise a H119Y variant *B. subtilis* dapA gene. The mutation was introduced by using the pTrc99A-BsdapA plasmid as a PCR template and amplifying with a pair of primers bsdapa119muts (SEQ ID NO: 5) and bsdapa119mutas (SEQ ID NO: 6). The nucleic acid sequence of SEQ ID NOS: 5 and 6 are shown below:

```
                                         SEQ ID NO: 5
(bsdapa119muts)    TCAAGAAGGAATGTACCAG TATTT CAAA

GCAATTGCGGCAGAGAC

SEQ ID NO: 6
(bsdapa119mutas)   GTCTCTGCCGCAATTGCTTT GAAAT ACTG

GTACATTCCTTCTTGA
```

The mutation sites on the primers are indicated by bold and italic characters.

*E. coli* DH5α competent cell was transformed with a aliquot of PCR product digested by DpnI. The plasmid was extracted from transformants and digested with restriction enzyme DraI to identify the desirable mutant plasmid pTrc99A-BsdapAH119Y, which comprised a nucleic acid sequence comprising two mutations from C to T at nucleotide residue 6019 and from T to C at nucleotide residue 6024 of SEQ ID NO: 1. The nucleic acid sequence encodes a protein having an amino acid sequence comprising a mutation from histidine to tyrosine at amino acid residue 119 of SEQ ID NO: 2.

Example 3

A Recombinant *E. Coli* Comprising a Wild Type *B. Subtilis* dapA Gene

A recombinant *E. coli* comprising a wild type *B. subtilis* dapA gene (DC051) was prepared from an *E. coli* bacterial strain DC037, which was received from Global Bio-Chem Technology Group Company Limited. DC037 carried two different plasmids, each containing a mutant dapA gene of *E. coli* and a tetracycline or kanamycin resistance gene. These two plasmids were knocked out and replaced with plasmids pDCtetBSdapA and pDCkanBSdapA, each containing a BsdapA gene and an tetracycline or kanamycin resistance gene as set forth blow.

Plasmid pDCtetBSdapA containing a BsdapA gene and a tetracycline resistance gene was constructed. BsdapA was obtained from pTrc99A-BsdapA by using a pair of primers, ptrcBSdapA1-F and ptrcBSdapA1-R having nucleic acid sequences as shown below in SEQ ID NOS: 7 and 8, respectively. A DNA fragment of 1.6 kb was recovered, and digested with restriction enzymes Tth111I and SpeI, and ligated with plasmid pDCtetdapA, which was previously digested with the same restriction enzymes, to prepare plasmid pDCtetBSdapA.

Plasmid pDCkanBSdapA containing a BsdapA gene and a kanamycin resistance gene was constructed. BsdapA was obtained from pTrc99A-BsdapA by using a pair of primers, ptrcBSdapA2-F and ptrcBSdapA2-R, having nucleic acid sequences as shown below in SEQ ID NOS: 9 and 10, respectively. A DNA fragment of 1.6 kb was recovered, and digested with restriction enzymes NotI and PshAI, and ligated with plasmid pDCkandapA, which was previously digested with the same restriction enzymes, to prepare plasmid pDCkanBSdapA.

DC045 was prepared from DC037. DC037 was treated with 800 μg/ml EB for 24 hours, subsequently screened by 5 μg/ml tetracycline and 50 μg/ml kanamycin, respectively, to prepare DC039, in which pDCkandapA was eliminated and pDCtetdapA remained.

A 2.8 kb fragment was obtained by amplifying *E. coli* W3110 with a pair of primers, LDCup and f1DN, having nucleic acid sequences as shown below in SEQ ID NOS: 11 and 12, respectively. This fragment was subcloned into the pMD18simple T vector to obtain pMD18swtLDC.

A 1.5 kb apramycin resistance gene was obtained by amplifying pIJ773 with a pair of primers, FRT5 and HPA1FRT3, having nucleic acid sequences as shown below in SEQ ID NOS: 13 and 14, respectively. pMD18swtLDC was digested by HpaI as a vector and ligated with 1.5 kb apramycin resistance gene fragment to obtain pMD18swtLDC-apra. A 4.5 kb fragment was isolated by digesting pMD18swtLDC-apra with PvuII and used as the recombinant fragment to transform DC039(pIJ790) to obtain DC043, in which wild type LDC was replaced with the truncated LDC in the genome of DC039. DC045 containing wild type LDC and plasmid pDCtetdapA was obtained after elimination of the apramycin resistance gene from the genome of DC043 with the help of plasmid pCP20.

Then, pDCamBSdapA was constructed to repulse the plasmid pDCtetdapA in DC045.

Plasmid pIJ773 was extracted and digested with restriction enzymes EcoRI and ClaI. A 1.3 kb fragment was isolated. A 3.4 kb fragment was obtained by digesting pDCtetBSdapA with restriction enzyme PvuII and was subsequently ligated with plasmid pMD18simple, which was previously digested with the same restriction enzyme to construct pMD18s (BStet) pMD18s(BStet) was digested with restriction enzymes EcoRI and ClaI to obtain a 4.5 kb fragment to be used as a vector. The 1.3 kb fragment obtained from pIJ773 was ligated with the 4.5 kb vector fragment. Competent DH5α cells were transformed with the ligation mixture and grown on ampicillin/apramycin containing plates. Plasmid DNA was extracted from the transformed bacteria and digested with restriction enzyme PvuII, and a fragment of 3.5 kb was obtained as a long-arm recombinant fragment.

BW25113(pIJ790) transformed with pDCtetBSdapA was further transformed with the long-arm recombinant fragment.

The recombinant plasmid pDCamBSdapA was extracted from the transformed bacteria, and used to transform DC045. Transformed DC045 contained two plasmids, pDCtetdapA and pDCamBSdapA. Due to repulsion of two replication origins, DC049-1 was obtained in which pDCtetdapA was removed and pDCamBSdapA remained. DC051 was obtained after transforming DC049-1 with pDCtetBSdapA and pDCkanBSdapA.

Bacteria of strain DC051 was deposited with the China General Microbiological Culture Collection Center (CGMCC) under the Budapest Treaty on Feb. 26, 2009, and given an accession number of CGMCC No. 2923.

DC073 having the expression vector pTrc99A was prepared similarly as a control. Unlike DC051, DC073 does not comprise pBsdapA.

The nucleic acid sequences of SEQ ID NOS: 7-14 are shown below:

```
                                                SEQ ID NO: 7
(ptrcBSdapA1-F) GGACACTGTCTAATGTGAGTTAGCGCG SEQ ID NO: 8
(ptrcBSdapA1-R) CACTAGTATTGAAGCATTTATCAGGGT

SEQ ID NO: 9
                GCGGCCGCTGTGCAGGTC

SEQ ID NO: 10
                GACCACTGTCAGGGTTATTGTCTCAT

SEQ ID NO: 11
(LDCup)         ATGAACATCATTGCCATTATGGG

SEQ ID NO: 12
(f1DN)          TTACTGCTCATACAGTTCCAACG

SEQ ID NO: 13
(FRT5)          ATTCCGGGGATCCGTCGACC

SEQ ID NO: 14
(HPA1FRT3)      AACAGCACGTTACTCGCCCGGAAGCCGC

TCTGGCAAGTTATGTAGGCTGGAGCTGC

TTC
```

DC051 and DC073 were grown in a cultivation medium with ampicillin at 37° C. for 3 days, and produced L-lysine in the medium at 150 and 20 grams per liter, respectively.

Example 4

A Recombinant *E. coli* Comprising a H119Y Variant *B. subtilis* dapA Gene

A recombinant *E. coli* comprising a H119Y variant dapA gene of *B. subtilis* (DC231) was prepared using the method described in Example 3 except that plasmid pTrc99A-BsdapAH119Y was used to replace plasmid pTrc99A-BsdapA. DC231 was obtained after transforming DC049-1 with pDCkanBSdapAH119Y and pDCtetBSdapAH119Y.

Bacteria of strain DC231 was deposited with the China General Microbiological Culture Collection Center (CGMCC) under the Budapest Treaty on Feb. 26, 2009, and given an accession number of CGMCC No. 2924.

DC231 was grown in a cultivation medium using the method described in Example 3. L-lysine was produced in the medium at 180 grams per liter.

INCORPORATION BY REFERENCE

All publications and patents mentioned herein are hereby incorporated by reference in their entirety as if each individual publication or patent were specifically and individually indicated to be incorporated by reference. In case of conflict, the present application, including any definitions herein, controls.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A recombinant DNA autonomously replicable in an *Escherichia coli* bacterium, wherein the recombinant DNA comprises a variant *B. subtilis* dapA gene comprising a nucleic acid sequence at least 90% identical to bases 5665-6537 of SEQ ID NO: 1 which comprises at least one mutation within bases 5665-6537 of SEQ ID NO: 1.

2. The recombinant DNA of claim 1, wherein the nucleic acid sequence comprises two mutations from C to T at nucleotide residue 6019 and from T to C at nucleotide residue 6024 of SEQ ID NO: 1.

3. The recombinant DNA of claim 1, wherein the variant dapA gene has a nucleic acid sequence that encodes a protein comprising an amino acid sequence at least 90% identical to SEQ ID NO: 2 which comprises at least one mutation within the amino acid sequence of SEQ ID NO:2.

4. The recombinant DNA of claim 3, wherein the amino acid sequence comprises a mutation from histidine to tyrosine at amino acid residue 119 of SEQ ID NO: 2.

5. An *Escherichia coli* bacterium comprising a variant *B. subtilis* dapA gene comprising a nucleic acid sequence at least 90% identical to bases 5665-6537 of SEQ ID NO: 1 which comprises at least one mutation within bases 5665-6537 of SEQ ID NO: 1, wherein the bacterium produces an increased amount of L-lysine as compared to a wild-type *Escherichia coli* bacterium.

6. The bacterium of claim 5, wherein the variant dapA gene has a nucleic acid sequence that encodes a protein comprising an amino acid sequence at least 90% identical to SEQ ID NO: 2 which comprises at least one mutation within the amino acid sequence of SEQ ID NO:2.

7. The bacterium of claim 5, wherein the bacterium has an accession number of CGMCC No. 2923 as deposited with the China General Microbiological Culture Collection Center.

8. The bacterium of claim 6, wherein the amino acid sequence comprises a mutation from histidine to tyrosine at amino acid residue 119 of SEQ ID NO: 2.

9. The bacterium of claim 5, wherein the bacterium has an accession number of CGMCC No. 2924 as deposited with the China General Microbiological Culture Collection Center.

10. The bacterium of claim 5, wherein the bacterium produces L-lysine at least 50 grams per liter in a cultivation medium.

11. A method for producing an increased amount of L-lysine as compared to a wild-type *Escherichia coli* bacterium comprising growing an *Escherichia coli* bacterium comprising a variant *B. subtilis* dapA gene comprising a nucleic acid sequence at least 90% identical to bases 5665-6537 of SEQ ID NO: 1 which comprises at least one mutation within bases 5665-6537 of SEQ ID NO: 1, in a cultivation medium, and collecting L-lysine from the cultivation medium.

12. The method of claim 11, wherein the variant dapA gene has a nucleic acid sequence that encodes a protein comprising an amino acid sequence at least 90% identical to SEQ ID NO: 2 which comprises at least one mutation within the amino acid sequence of SEQ ID NO:2.

13. The method of claim 12, wherein the amino acid sequence comprises a mutation from histidine to tyrosine at amino acid residue 119 of SEQ ID NO: 2.

* * * * *